United States Patent
James et al.

(10) Patent No.: US 9,388,194 B2
(45) Date of Patent: Jul. 12, 2016

(54) ACRYLIC COMPOUND HAVING TETRAOXASPIRO BACKBONE FOR RADIATION CURING COMPOSITIONS

(71) Applicant: Perstorp AB, Perstorp (SE)

(72) Inventors: David James, Hassleholm (SE); Linda Zellner, Helsingborg (SE)

(73) Assignee: PERSTORP AB, Perstorp (SE)

( * ) Notice: Subject to any disclaimer, the term of this patent is extended or adjusted under 35 U.S.C. 154(b) by 0 days.

(21) Appl. No.: 14/785,771

(22) PCT Filed: Jan. 15, 2014

(86) PCT No.: PCT/SE2014/000003
§ 371 (c)(1),
(2) Date: Oct. 20, 2015

(87) PCT Pub. No.: WO2014/175801
PCT Pub. Date: Oct. 30, 2014

(65) Prior Publication Data
US 2016/0075717 A1    Mar. 17, 2016

(30) Foreign Application Priority Data
Apr. 22, 2013   (SE) ...................................... 1300291

(51) Int. Cl.
*C07D 493/10*    (2006.01)

(52) U.S. Cl.
CPC .................................. *C07D 493/10* (2013.01)

(58) Field of Classification Search
CPC ....................................................... C07D 493/10
See application file for complete search history.

(56) References Cited

U.S. PATENT DOCUMENTS

| | | | |
|---|---|---|---|
| 3,931,353 A | 1/1976 | Hanyuda et al. | |
| 3,933,857 A | 1/1976 | Hanyuda et al. | |
| 4,579,925 A | 4/1986 | Ueno et al. | |
| 8,632,866 B2* | 1/2014 | Ikeda | ..................... B32B 27/08 428/34.1 |
| 2008/0200582 A1 | 8/2008 | Craciun et al. | |

FOREIGN PATENT DOCUMENTS

JP       S57102891 A      6/1982

OTHER PUBLICATIONS

International Search Report Dated Apr. 7, 2014.

\* cited by examiner

*Primary Examiner* — Golam M M Shameem
(74) *Attorney, Agent, or Firm* — Polsinelli PC

(57) ABSTRACT

Disclosed is a process for obtaining an acrylic compound having a tertaoxaspiro backbone and at least one acrylic unsaturation. Said compound is in embodiments an acrylate, a methacrylate or a crotonate of an alkoxylated, such as an ethoxylated, a propoxylated and/or a butoxylated 2,4,8,10-tetraoxaspiro[5.5]undecane3,9-dialkanol.

11 Claims, No Drawings

ACRYLIC COMPOUND HAVING TETRAOXASPIRO BACKBONE FOR RADIATION CURING COMPOSITIONS

CROSS REFERENCE TO RELATED APPLICATIONS

This application is a 35 U.S.C. §371 National Stage application of International Application PCT/SE2014/000003 filed Jan. 15, 2014, which in turn, claims priority of Swedish Application No. 1300291-0, filed Apr. 22, 2013, the entire disclosures of which are herein incorporated by reference.

The present invention refers to a process for production of an acrylic compound, more specifically an acrylated, a methacrylated and/or a crotonated (methylacrylated) 2,4,8,10-tetraoxaspiro[5.5]-undecane-3,9-dialkanol alkoxylate.

Chemical compounds having one or more acrylic unsaturations are well known in the art and used as reactants and chemical building blocks in a wide variety of applications, such as drying and/or heat curing and/or UV, IR and EB curing paints, enamels, putties, lacquers, varnishes, adhesives and inks, esters and polyesters, latex, fibres, textiles and so on, as well as in for instance moulding and casting compositions and the like. There is, however, despite the large amount of commercially available acrylic compounds and derivatives thereof, due to for instance environmental concerns and legislation and/or new application areas, a substantial and ever growing demand for novel, safer, more efficient and/or more versatile compounds having one or more acrylic double bonds.

A major search, for safer acrylic compounds for use in polymeric materials, is directed to suitable replacements for presently used acrylic compounds based on bisphenols and alkoxylated bisphenols, such as the frequently used ethoxylated bisphenol A. Bisphenols and derivatives thereof are known to be endocrine disrupters that mimic for instance oestrogen and are associated with irritation to respiratory system, risks of serious damage to the eyes and neural system, risk of sensitisation by skin contact and risk of impaired fertility. The hazardous effects of inadvertent exposure to bisphenols and bisphenol releasing chemicals in professionals and the general populations should thus be avoided.

An object of the present invention is to provide a novel acrylic compound having at least one acrylic double bond. A further object is to provide a suitable replacement for acrylic compounds based on said bisphenols especially alkoxylated bisphenols. Yet a further object is to provide a suitable replacement for acrylic compounds involving handling of hazardous and restricted compounds, such as unsaturated, acrylic, cycloacetal compounds as disclosed in for instance U.S. Pat. No. 3,933,857. The in said publication. disclosed compounds are obtained by reacting pentaerythritol or sorbitol with acrolein and subsequently reacting obtained diallylidene pentaerythritol or triallylidene sorbitol on the double bonds with a hydroxyacrylate, such as hydroxyethyl acrylate or trimethylolpropane diacrylate. Preparation of these compounds involves handling of the hazardous and restricted compound acrolein.

It has now quite unexpectedly been found that a compound versatile in most applications involving compounds and reactants having acrylic unsaturation, such as said alkoxylated bisphenols and said allylidene based compounds, can be obtained by alkoxylating a 2,4,8,10-tetraoxaspiro-[5.5]undecane-3,9-dialkanol and subsequently acrylating obtained 2,4,8,10-tetraoxaspiro-[5.5]undecane-3,9-dialkanol alkoxylate. The novel acrylic compound of the present invention can thus advantageously replace said compounds as a product being safer to handle, safer to produce and/or being environmentally friendlier.

The novel acrylic compound of the present invention has at least one acrylic double bond and is obtained by subjecting a 2,4,8,10-tetraoxaspiro[5.5]undecane-3,9-dialkanol to alkoxylation yielding a 2,4,8,10-tetraoxaspiro[5.5]undecane-3,9-dialkanol alkoxylate having one or more alkoxy unit(s)/molecule, and subsequently subjecting said 2,4,8,10-tetraoxaspiro-[5.5]undecane-3,9-dialkanol alkoxylate to acrylation by reaction with an acrylic compound yielding an acrylated 2,4,8,10-tetraoxaspiro[5.5]undecane-3,9-dialkanol alkoxylate having at least one acrylic double bond.

Embodiments of said acrylic compound includes acrylic acid, methacrylic acid and/or a crotonic acid (crotonic and isocrotonic acid) as well as corresponding halides or alkylesters, such as methyl and ethyl esters.

The acrylic compound of the present invention is in preferred embodiments a mono or diacrylate, a mono or dimethacrylate or a mono or dicrotonate of an alkoxylated 2,4,8,10-tetraoxaspiro[5.5]undecane-3,9-dialkanol alkoxylate having for instance 1-10, 1-8, 1-6, 1-4 or most preferably 3-6 alkoxy, such as ethoxy, propoxy and/or butoxy, unit(s)/molecule.

The 2,4,8,10-tetraoxaspiro[5.5]undecane-3,9-dialkanol is in embodiments of the present invention a compound of Formula (1)

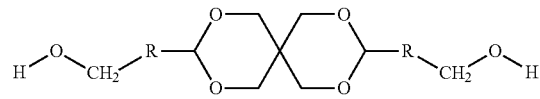

wherein substituent R is a linear or branched $C_1$-$C_8$ alkyl group. The most preferred embodiment of said 2,4,8,10-tetraoxaspiro[5.5]undecane-3,9-dialkanol is 2,4,8,10-tetraoxaspiro[5.5]-undecane-3,9-diethanol (pentaerythritol spiroglycol).

Especially preferred embodiments of the present invention includes, but are not limited to, a mono or diacrylate, a mono or dimethacrylate and/or a mono or dicrotonate of a 2,4,8,10-tetraoxaspiro[5.5]undecane-3,9-diethanol ethoxylate and/or propoxylate, such as a diacrylate, a dimethacrylate and/or a dicrotonate of a 2,4,8,10-tetraoxaspiro[5.5]undecane-3,9-diethanol ethoxylate (pentaerythritol spiroglycol ethoxylate and/or propoxylate) having for instance 3-6 ethoxy and/or propoxy units.

In a further aspect, the present invention refers to a process for production of an acrylic compound as disclosed above. The process comprises the Steps of i) subjecting a 2,4,8,10-tetraoxaspiro[5.5]undecane-3,9-dialkanol to alkoxylation with an alkylene oxide yielding a 2,4,8,10-tetraoxaspiro[5.5]undecane-3,9-dialkanol alkoxylate, having one or more alkoxy unit(s)/molecule, such as previously disclosed 1-10, 1-8, 1-6, 1-4 or 3-6 alkoxy unit(s)/molecule, and ii) subjecting in Step (i) yielded 2,4,8,10-tetraoxaspiro[5.5]undecane-3,9-dialkanol alkoxylate or a pre-produced 2,4,8,10-tetraoxaspiro[5.5]undecane-3,9-dialkanol alkoxylate to acrylation by either (a) esterification with acrylic acid, methacrylic acid and/or a crotonic acid or (b) transesterification with an alkylacrylate, an alkylmethacrylate and/or an alkylcrotonate, said esterification or transesterification yielding an acrylated 2,4,8,10-tetraoxaspiro[5.5]undecane-3,9-dialkanol alkoxylate having at least one acrylic double bond.

Said 2,4,8,10-tetraoxaspiro[5.5]undecane-3,9-dialkanol alkoxylate can be produced by alkoxylation, using procedures and reactants commonly known in the art, such as said reaction with an alkylene oxide, such as ethylene, propylene and/or butylene oxide or alternatively by reaction with a corresponding glycol, such as ethylene glycol, propylene glycol and/or butylene glycol, yielding alkoxylates having for instance one or more ethoxy, propoxy and/or butoxy unit(s)/molecule.

Preferred embodiments of said 2,4,8,10-tetraoxaspiro[5.5]undecane-3,9-dialkanol are as previously disclosed by Formula (I), such as said 2,4,8,10-tetraoxaspiro[5.5]undecane-3,9-diethanol (pentaerythritol spiroglycol).

The 2,4,8,10-tetraoxaspiro[5.5]undecane-3,9-dialkanol alkoxylate can be acrylated using any procedure commonly known in the art, such as direct esterification with acrylic acid, methacrylic acid and/or a crotonic acid or by transesterification with an alkylacrylate, alkylmethacrylate and/or alkylcrotonate, yielding an acrylate, a methacrylate and/or a crotonate, having at least one acrylic double bond, according to embodiments of the present invention as previously disclosed and defined. Suitable acrylation agents include, but are not limited to, acrylic acid, methacrylic acid and crotonic acids—crotonic and isocrotonic acid—as well as corresponding alkyl, such as methyl or ethyl, esters and corresponding halides, such as chlorides, bromides and iodides.

In preferred embodiments of the process according to the present invention, Step (i) yields a 2,4,8,10-tetraoxaspiro[5.5]undecane-3,9-diethanol ethoxylate and/or propoxylate, and Step (ii) yields a mono or diacrylate, a mono or dimethacrylate or a mono or dicrotonate.

In the most preferred embodiments of the process according to the present invention, Step (i) yields a 2,4,8,10-tetraoxaspiro[5.5]undecane-3,9-diethanol ethoxylate and/or propoxylate having 3-6 ethoxy and/or propoxy units/molecule and Step (ii) yields a diacrylate, a dimethacrylate or a dicrotonate.

In yet further aspects, the present invention refers to an acrylate produced by the process disclosed and defined above and to the use of an acrylic compound, as disclosed and defined above, and/or to the use of an acrylic compound produced by the process, as disclosed and defined above, for production of a radiation, such as ultraviolet (UV), curing lacquer, varnish, paint, enamel, putty, prototyping, including rapid prototyping, composition, ink, including printing ink, or adhesive.

Without further elaboration, it is believed that one skilled in the art can, using the preceding description, utilise the present invention to its fullest extent. The following preferred specific embodiments are, therefore, to he construed as merely illustrative and not limitative. In the following Example 1 illustrate alkoxylation (ethoxylation) of 2,4,8,10-tetraoxaspiro[5.5]-undecane-3,9-diethanol and Examples 2-3 illustrate preparation of acrylates according to embodiments of the present invention and Example 5 refers to preparation of a coating formulation comprising the acrylate yielded in Example 2 and a comparative coating formulation comprising a comparative Bisphenol A ethoxylate acrylate. Example 6 reports results from curing and testing of cured films obtained from the coating formulations prepared in Example 5.

EXAMPLE 1

2,4,8,10-tetraoxaspiro[5.5]undecane-3,9-diethanol (pentaerythritol spiroglycol, Perstorp Specialty Chemicals AB, Sweden) was together with KOH as catalyst and dimethylformamide as solvent charged in reaction vessel. The mixture was stirred and heated to 150° C. A nitrogen purge was used. Ethylene oxide (molar ratio spiroglycol to ethylene oxide of 1:5) was at 150° C. and a pressure of 2500-4000 mm Hg, charged during 2 hours. A nitrogen purge was used and the temperature of 150° C. was maintained for a further 30 minutes after which time unreacted ethylene oxide was evaporated at 150° C. and <1 mm Hg. Finally the product was stabilised by addition of 250 ppm of butylhydroxytoluene (BHT).

Yielded product was by gas chromatographic (GC) analysis evidenced to he ethoxylated 2,4,8,10-tetraoxaspiro[5.5]undecane-3,9-diethanol having an average of 4-5 ethoxy units/molecule. The hydroxyl value was 209 mg KOH/g.

EXAMPLE 2

100.0 parts by weight of the ethoxylated 2,4,8,10-tetraoxaspiro[5.5]undecane-3,9-diethanol yielded in Example 1 was subjected to esterification with 31.4 parts by weight of acrylic acid (excess of acrylic acid 10% by weight). 1.3 parts by weight of p-toluenesulphonic acid was used as catalyst, 0.2 parts by weight of methoxy phenol was used as inhibitor and 100.0 parts by weight of toluene was used as azeotropic solvent. All compounds were charged to a reaction vessel equipped with a heating device, temperature control, agitation and reflux. The temperature was raised to 140° C. and maintained until the esterification was completed—reaction time 23 hours. Yielded reaction mixture was subsequently cooled and toluene and excess acrylic acid were evaporated. Obtained product was neutralised to pH 6-8 with 3% of sodium hydrogenphosphate together with 1.5% of water and 1.5% of a filter aid (Celite), calculated on charged raw materials. The water was after one hour of stirring at 120° C. evaporated during 30 minutes at said temperature and at a vacuum of <1 mm Hg. Finally, the product was filtered at 100° C.

Yielded product was by gas chromatographic (GC) analysis evidenced to be diacrylated 2,4,8,10-tetraoxaspiro[5.5]undecane-3,9-diethanol ethoxylate.

EXAMPLE 3

Example 2 was repeated with the difference that methacrylic acid was used instead of acrylic acid at the same ratio hydroxyl groups to acid groups (10% excess —COOH).

Yielded product was by gas chromatographic (GC) analysis evidenced to be dimethacrylated 2,4,8,10-tetraoxaspiro[5.5]undecane-3,9-diethanol ethoxylate.

EXAMPLE 4

Example 2 was repeated with the difference that crotonic acid (β-methylacrylic acid) was used instead of acrylic acid at the same ratio hydroxyl groups to acid groups (10% excess —COOH).

Yielded product was by gas chromatographic (GC) analysis evidenced to be dicrotonated 2,4,8,10-tetraoxaspiro[5.5]undecane-3,9-diethanol ethoxylate.

EXAMPLE 5

The diacrylate of Example 2 (PSG eo diacrylate) was evaluated in a UV-curing lacquer composition and compared with a corresponding (comparative) bisphenol A ethoxylate diacrylate (BPA eo diacrylate) having an average of 4 ethoxy units/phenolic hydroxyl group (Sigma Aldrich Co).

Coating formulations (weight percentage):

|  | Example 2 | Comparative |
| --- | --- | --- |
| PSG eo diacrylate | 50 | — |
| BPA eo diacrylate | — | 50 |
| Hexanediol diacrylate | 10 | 10 |
| Tripropylene diacrylate | 36 | 36 |
| Irgacure ® 500 * | 4 | 4 |
| Viscosity, mPas | 80 | 100 |

* Photoinitiator (Ciba Specialty Chemicals Inc.)

EXAMPLE 6

The UV-curing lacquers prepared in Example 4 were coated on glass and steel panels at a dry filmthickness of 15±2 µm and were cured by means of a UV-lamp of 80 W/cm² and at a belt speed of 20 m/min. The lacquers were allowed to pass the UV-lamp 4 times. The samples were after curing conditioned for 24 hours at 23±2° C. and at 50±5% relative humidity followed by measuring of filmhardness, flexibility and gloss. The resistance to water after 4 passages under the UV-lamp was conducted during 120 hours and evaluated according to Swedish Standard SS 839118 on a scale of 0-5, wherein 5 is best. The resistance to acetone was evaluated by placing acetone, soaked into a small piece of filtre paper and placed under a small cup, on the film surface and time until damaged film was recorded.

Recorded results:

|  | Example 1 | Comparative |
| --- | --- | --- |
| Hardness, König secs. | 98 | 98 |
| Pencil hardness | F-H | F-H |
| Erichsen flexibility, mm | 4.0 | 3.9 |
| Gloss at 60° | 88 | 95 |
| Water, scale | 3 | 3 |
| Acetone, minutes | 10 | 10 |

The invention claimed is:

1. A process for obtaining a compound having a tetraoxaspiro backbone and at least one acrylic double bond characterised in, that said process comprises the Steps of
   i) subjecting a 2,4,8,10-tetraoxaspiro[5.5]undecane-3,9-dialkanol to alkoxylation with an alkylene oxide yielding a 2,4,8,10-tetraoxaspiro[5.5]undecane-3,9-dialkanol alkoxylate having one or more alkoxy unit(s)/molecule, and
   ii) subjecting in Step (i) yielded 2,4,8,10-tetraoxaspiro[5.5]undecane-3,9-dialkanol alkoxylate or a pre-produced 2,4,8,10-tetraoxaspiro[5.5]undecane-3,9-dialkanol alkoxylate to acrylation by either (a) esterification with acrylic acid, methacrylic acid and/or a crotonic acid or (b) transesterification with an alkylacrylate, an alkylmethacrylate and/or an alkylcrotonate, said esterification or transesterification yielding an acrylated 2,4,8,10-tetraoxaspiro[5.5]undecane-3-9-dialkanol alkoxylate having at least one acrylic double bond.

2. The process according to claim 1, wherein said alkylacrylate, alkylmethacrylate and/or alkylcrotonate is methylacrylate, ethylacrylate, methylmethacrylate, ethylmethacrylate, a methylcrotonate and/or an ethylcrotonate.

3. The process according to claim 1 wherein Step (i) yields a 2,4,8,10-tetraoxaspiro[5.5]undecane-3,9-dialkanol alkoxylate having 1-8 alkoxy unit(s)/molecule.

4. The process according to claim 1 wherein Step (i) yields a 2,4,8,10-tetraoxaspiro[5.5]undecane-3,9-dialkanol alkoxylate having 1-6 alkoxy unit(s)/molecule.

5. The process according to claim 1 wherein Step (i) yields a 2,4,8,10-tetraoxaspiro[5.5]undecane-3,9-dialkanol alkoxylate having 1-4 alkoxy unit(s)/molecule.

6. The process according to claim 1, wherein said alkylene oxide is ethylene oxide, propylene oxide and/or butylene oxide and said alkoxy unit(s) is/are ethoxy, propoxy and/or butoxy.

7. The process according to claim 1, wherein said 2,4,8,10-tetraoxaspiro[5.5]undecane-3,9-dialkanol is 2,4,8,10-tetraoxaspiro[5.5]-undecane-3,9-diethanol.

8. The process according to claim 1, wherein Step (i) yields a 2,4,8,10-tetraoxaspiro[5.5]undecane-3,9-diethanol ethoxylate and/or propoxylate.

9. The process according to claim 1, wherein said Step (ii) yields a mono or diacrylate, a mono or dimethacrylate or a mono or dicrotonate.

10. The process according to claim 1, wherein Step (i) yields a 2,4,8,10-tetraoxaspiro[5.5]undecane-3,9-diethanol ethoxylate having 4-5 ethoxy unit(s)/molecule and that Step (ii) yields a diacrylate, a dimethacrylate or a dicrotonate.

11. Method of forming an acrylic compound according to claim 1 for production of a radiation curing composition selected from the group consisting of a UV curing lacquer, a UV curing varnish, a UV curing paint, a UV curing enamel, a UV curing putty, a UV curing prototyping composition, a UV curing ink, and a UV curing adhesive.

* * * * *